US00PP27559P2

(12) United States Plant Patent
Moore

(10) Patent No.: US PP27,559 P2
(45) Date of Patent: Jan. 17, 2017

(54) ***ANTIRRHINUM* PLANT NAMED 'PMOORE07'**

(50) Latin Name: *Antirrhinum majus*
Varietal Denomination: Pmoore07

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 73 days.

(21) Appl. No.: 14/545,538

(22) Filed: May 18, 2015

(51) Int. Cl.
*A01H 5/02* (2006.01)

(52) U.S. Cl.
USPC ..... Plt./322

(58) Field of Classification Search
USPC ..... Plt./322
See application file for complete search history.

(56) References Cited

PUBLICATIONS

UPOV hit on *antirrhinum* 'Pmoore07', QZ PBR 42310, published Dec. 15, 2014.*

* cited by examiner

*Primary Examiner* — Anne Grunberg
(74) *Attorney, Agent, or Firm* — Penny J. Aguirre

(57) ABSTRACT

A new cultivar of *Antirrhinum*, 'Pmoore07', that is characterized by its compact, upright plant habit, its extended bloom season, its narrow, elongated flowers that are purple-pink in color with a whitish yellow throat, and its increased resistant to fungal diseases, especially, *Puccinia antirrhini* (leaf rust) as compared to other *Antirrhinum* cultivars.

2 Drawing Sheets

Botanical classification: *Antirrhinum majus*.
Cultivar designation: 'Pmoore07'.

BACKGROUND OF THE INVENTION

The present invention relates to a new and distinct cultivar of *Antirrhinum majus* and will be referred to hereafter by its cultivar name, 'Pmoore07'. 'Pmoore07' represents a new snapdragon, a half-hardy herbaceous perennial typically grown as an annual.

The new cultivar was derived from a controlled breeding program by the Inventor in Longstock, England. The objective of the breeding program is to develop new cultivars of *Antirrhinum* that are more disease resistant and produce unique plant forms and flower colors. The Inventor made a cross in July of 2010 between *Antirrhinum majus* 'Eve Grey' (not patented) as the female parent and an unnamed proprietary plant of *Antirrhinum majus* subsp. *tortuosum* from the Inventor's breeding program as the male parent. The Inventor selected 'Pmoore07' in August of 2011 as a single unique plant amongst the seedlings that resulted from the above cross.

Asexual propagation of the new cultivar was first accomplished by the Inventor via softwood stem cuttings in October of 2011 in Longstock, England. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pmoore07' as a unique cultivar of *Antirrhinum*.

1. 'Pmoore07' exhibits a compact, upright plant habit.
2. 'Pmoore07' exhibits an extended bloom season, flowering from early July until first frost, with deadheading, in England.
3. 'Pmoore07' exhibits narrow, elongated flowers that are purple-pink in color with a whitish yellow throat (Penstemon-like).
4. 'Pmoore07' exhibits increased resistant to fungal diseases, especially, *Puccinia antirrhini* (leaf rust) as compared to other *Antirrhinum* cultivars.

The female parent of 'Pmoore07', 'Eve Grey', differs from 'Pmoore07' in having flowers that are less pink in color, in being more susceptible to fungal diseases, and in having a flowering period that is shorting in length. The male parent of 'Pmoore07' differs from 'Pmoore07' in having a more open plant habit and in having differently shaped flowers. 'Pmoore07' can be most closely compared to the *Antirrhinum* cultivars 'Liberty Pink' (not patented) and 'Rocket Pink' (not patented). 'Liberty Pink' differs from 'Pmoore07' in being larger in overall size, in having an earlier commencing bloom season, and in having flowers that are light pink in color. 'Rocket Pink' differs from 'Pmoore07' in being smaller in overall size, in having a spreading plant habit, and in having flowers that are deep pink in color.

BRIEF DESCRIPTION OF THE DRAWINGS

The accompanying colored photographs illustrate the overall appearance and distinct characteristics of the new *Antirrhinnum*. The photographs were taken of a plant about 18 months in age as grown outdoors in a 7.5-liter container in Stockbridge, England.

The photograph in FIG. 1 provides a side view of 'Pmoore07' in bloom.

Figure 1:
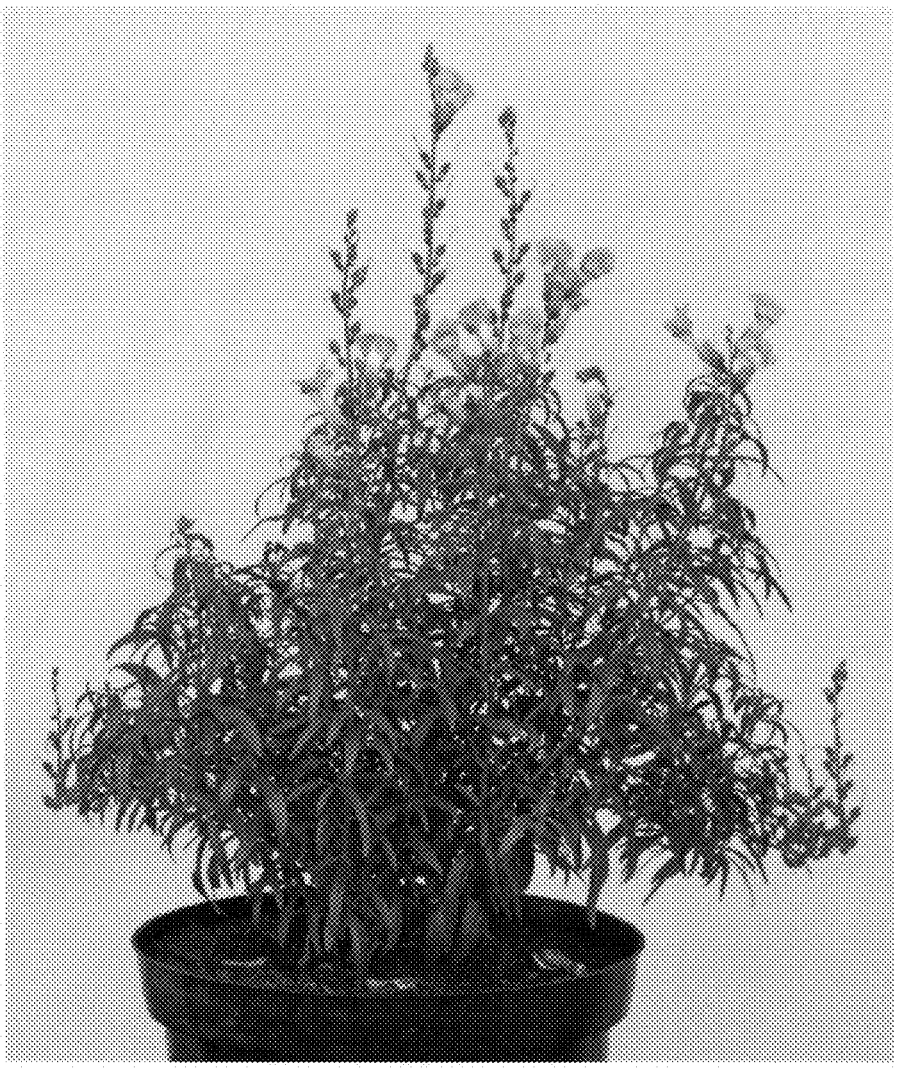
Figure 2:
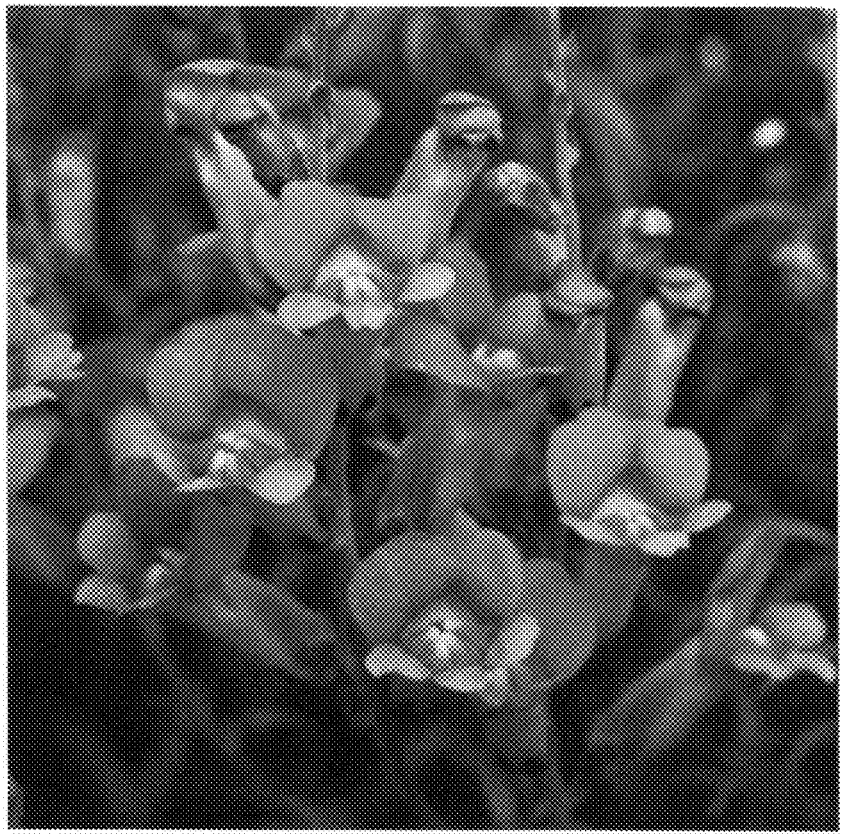

The photograph in FIG. 2 provides a close-up view of an inflorescence of 'Pmoore07'.

Figure 3:
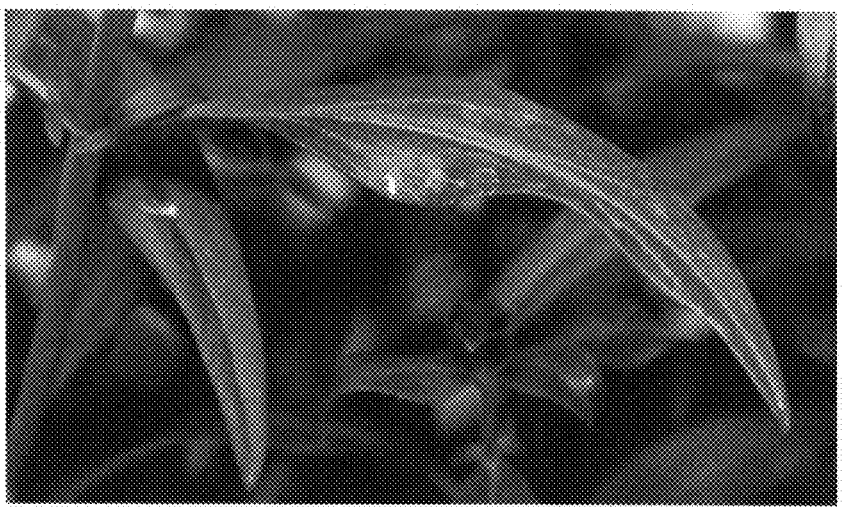

The photograph in FIG. 3 provides a close-up view of the foliage of 'Pmoore07'.

The colors in the photographs are as close as possible with the photographic and printing technology utilized and the color values cited in the Detailed Botanical Description accurately describe the colors of the new *Antirrhinum*.

DETAILED BOTANICAL DESCRIPTION OF THE PLANT

The following is a detailed description of plants about 18 months in age as grown outdoors in 7.5-liter containers in October in Stockbridge, England. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From early July until first frost, with deadheading, in England.

*Plant type*.—Herbaceous perennial.

*Plant habit*.—Compact, upright.

*Height and spread*.—An average of 47 cm in height and 38 cm in spread.

*Cold hardiness*.—At least to U.S.D.A. Zone 6, an take occasional frosts to −8° C.

*Diseases and pests*.—Resistance has been observed to fungal diseases, especially *Puccinia antirrhini* (leaf rust) as compared to other *Antirrhinum* cultivars grown under similar conditions.

*Root description*.—Fibrous.

*Propagation*.—Softwood stem cuttings.

*Growth rate*.—Moderate.

Stem description:

*Branch habit*.—Main stems grow from the base and have lateral branches, an average of 4 main stems and 10 lateral branches per main stem.

*Stem size*.—An average of 16 cm in length and 2.5 mm in width.

*Stem shape*.—Rounded.

*Stem color*.—137B to 137C.

*Stem surface*.—Glossy.

*Stem strength*.—Moderately weak.

*Stem aspect*.—Held at an average angle of 37.5° to main stems.

*Internode length*.—An average of 2 cm in length.

Foliage description:

*Leaf shape*.—Narrow elliptic to lanceolate.

*Leaf division*.—Simple with numerous leaves of various sizes from the same node.

*Leaf base*.—Long attenuate.

*Leaf apex*.—Acute.

*Leaf size*.—An average of 5 cm in length and 0.75 mm in width.

*Leaf venation*.—Pinnate, inconspicuous, the same color as the leaf surface.

*Leaf margins*.—Entire.

*Leaf attachment*.—Sessile.

*Leaf arrangement*.—Whorled.

*Leaf surface*.—Upper and lower surfaces; dull and glabrous.

*Leaf color*.—Upper surface; 139A and lower surface; 134A.

*Leaf number*.—Dense, an average of 50 mature leaves per lateral branch 16 cm in length.

*Leaf aspect*.—Moderately recurved.

Flower description:

*Inflorescence type*.—Terminal racemes of bilabiate flowers, blooms from the base to the apex.

*Inflorescence size*.—An average of 16.4 cm in length and 5.2 mm in width.

*Lastingness of flower*.—About 5 days, not persistent.

*Flower size*.—An average of 4 cm in depth and 2.3 cm in diameter.

*Flower fragrance*.—None.

*Flower aspect*.—Upright and outward.

*Flower number per inflorescence*.—An average of 18 flowers per flowering spike.

*Peduncle*.—Rounded in shape, an average of 16 cm in length and 2 mm in width, moderate strength, 138B in color, held at an average angle of 0° to lateral stem, flower internode length is an average of 1.5 cm.

*Pedicel*.—Rounded in shape, an average of 6 mm in length and 1 mm in width, moderate strength, color; 143A suffused with 184B at the tip, held at an average angle of 45° to the peduncle.

*Flower buds*.—Broad oblong in shape, an average of 8 mm in length and 0.5 mm in diameter, color; petal portion 145A with tip 152A and calyx portion 147B.

*Flower type*.—Zygomorphic and bilabiate, held at an average angle of 40° to peduncle.

*Calyx*.—Campanulate and rotate, an average of 5 mm in length and 8 mm in diameter.

*Sepals*.—5, rotate, ovate in shape with lower 20% fused, entire margin, acute apex, fused broadly cuneate base, an average of 5 mm in width and 3 mm in length, color immature upper surface 144A and lower surface 147B, mature upper surface 143A and lower surface 148A, both surfaces dull and densely covered with short glandular hairs an average of 0.4 mm in length and NN155D in color.

*Corolla features*.—Bilabiate with lower 58% fused to tube, upper lip; comprised of 2 orbicular shaped lobes that are folded outwards, an average of 3.8 cm in length and 2.3 cm in width, lower lip; comprised of 3 orbicular shaped lobes that are folded outwards, an average of 3.8 cm in length and 2 cm in width, upper and lower lip petals; entire margin, obtuse apex, color; upper surface of both lips when opening and when fully open N74C with base and tubes N155A to N155B, base of tube is suffused with 72B and has 4 pubescent calluses an average of 9 mm in length and 1 mm in width and 7A in color, lower lip has a small dot near the base 2C in color, lower surface of both lips when opening and when fully open a blend between 70B and N74C with base of tube 70A to 70B and tip 75C, petal color fades to 72A to 72B, other than calluses on tube, all other surfaces are glabrous.

Reproductive organs:

*Gynoecium.*—1 pistil, an average of 1.7 cm in length, style is an average of 1.6 cm in length and 182C in color, stigma is club-shaped and 144B to 144C in color, ovary is superior and 152D in color.

*Androcoecium.*—4 stamens, filament is an average of 2.1 cm in length and 75C to 75D with NN155D at the tip in color, paired basifixed anther is elliptic in shape, an average of 1.5 mm in length and 13C in color, pollen is moderate in quantity and 13B in color.

*Fruit and seed.*—None observed.

It is claimed:

1. A new and distinct cultivar of *Antirrhinum* plant named 'Pmoore07' as herein illustrated and described.

* * * * *